(12) United States Patent
Hsien et al.

(10) Patent No.: US 11,998,429 B1
(45) Date of Patent: Jun. 4, 2024

(54) REUSABLE MENSTRUAL PAD

(71) Applicants: Chi Chen Hsien, Sacramento, CA (US); Thomas C Chan, Palo Alto, CA (US)

(72) Inventors: Chi Chen Hsien, Sacramento, CA (US); Thomas C Chan, Palo Alto, CA (US)

( * ) Notice: Subject to any disclaimer, the term of this patent is extended or adjusted under 35 U.S.C. 154(b) by 0 days.

(21) Appl. No.: 18/521,193

(22) Filed: Nov. 28, 2023

(51) Int. Cl.
*A61F 13/15* (2006.01)
*A61F 13/472* (2006.01)
*A61F 13/505* (2006.01)
*A61F 13/511* (2006.01)
*A61F 13/513* (2006.01)

(52) U.S. Cl.
CPC ...... *A61F 13/505* (2013.01); *A61F 13/15577* (2013.01); *A61F 13/472* (2013.01); *A61F 13/51121* (2013.01); *A61F 2013/51383* (2013.01)

(58) Field of Classification Search
CPC .............. A61F 13/505; A61F 13/15577; A61F 13/51121; A61F 13/472; A61F 13/47; A61F 13/5616; A61F 13/476; A61F 2013/51383; A61F 2013/15276
See application file for complete search history.

(56) References Cited

U.S. PATENT DOCUMENTS

| | | | |
|---|---|---|---|
| 6,764,477 B1* | 7/2004 | Chen | A61F 13/4702 604/385.19 |
| 2006/0004340 A1* | 1/2006 | Ben-Natan | C08L 83/04 604/385.19 |
| 2017/0354549 A1* | 12/2017 | Cho | A61F 13/472 |
| 2018/0369029 A1* | 12/2018 | Barnhorst | A61F 13/51456 |

* cited by examiner

*Primary Examiner* — Jacqueline F Stephens
(74) *Attorney, Agent, or Firm* — Silicon Valley Patent Group LLP; Thomas C. Chan

(57) ABSTRACT

Apparatuses of reusable menstrual pad and methods for manufacturing the same are provided. In one embodiment, a menstrual pad includes an interior layer includes an excretion area, where the excretion area includes an opening configured to drain menstrual fluid of a user away from the interior layer; a middle layer configured to house a menstrual fluid collection unit, where the menstrual fluid collection unit is configured to sanitize the menstrual fluid drained from the interior layer and to store the sanitized menstrual fluid to one or more menstrual napkins in the middle layer; an exterior layer configured to conceal and prevent leakage from the middle layer of the menstrual pad; and a support frame configured to hold the interior layer, the middle layer and the exterior layer of the menstrual pad together.

20 Claims, 9 Drawing Sheets

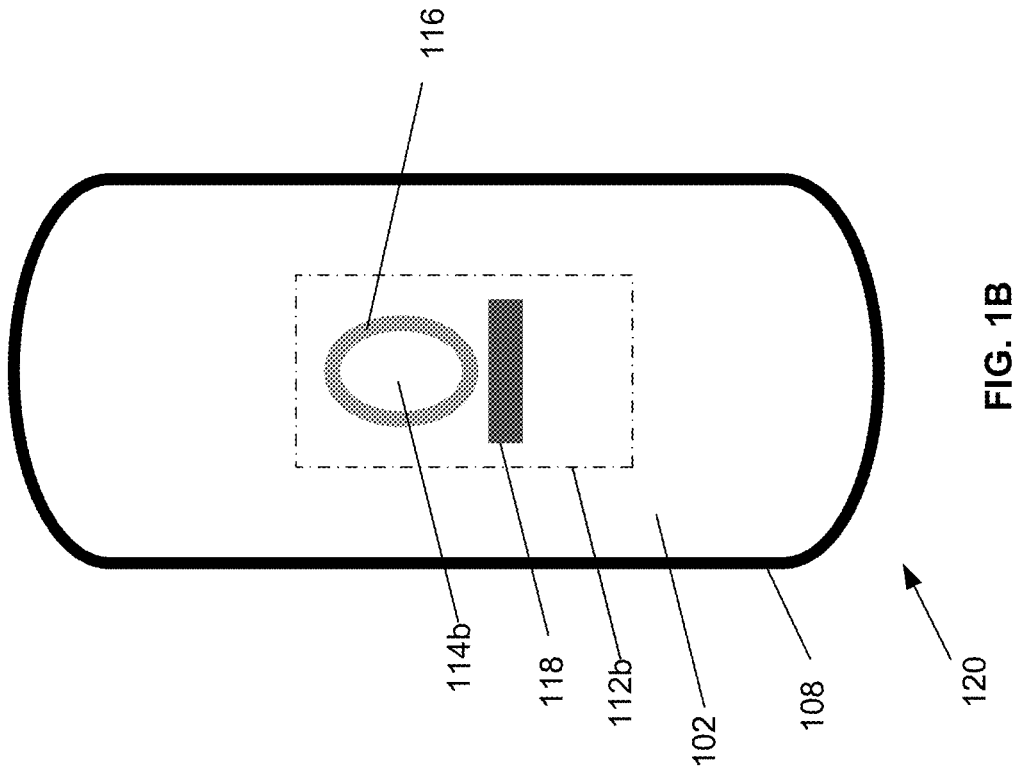
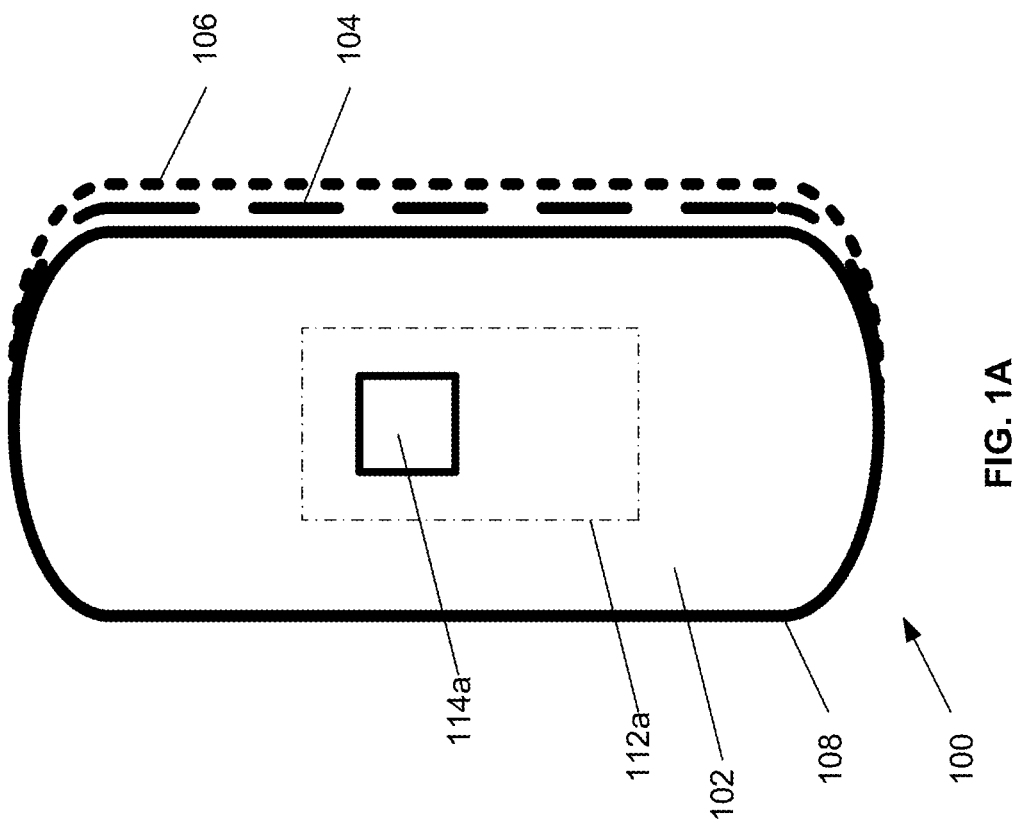

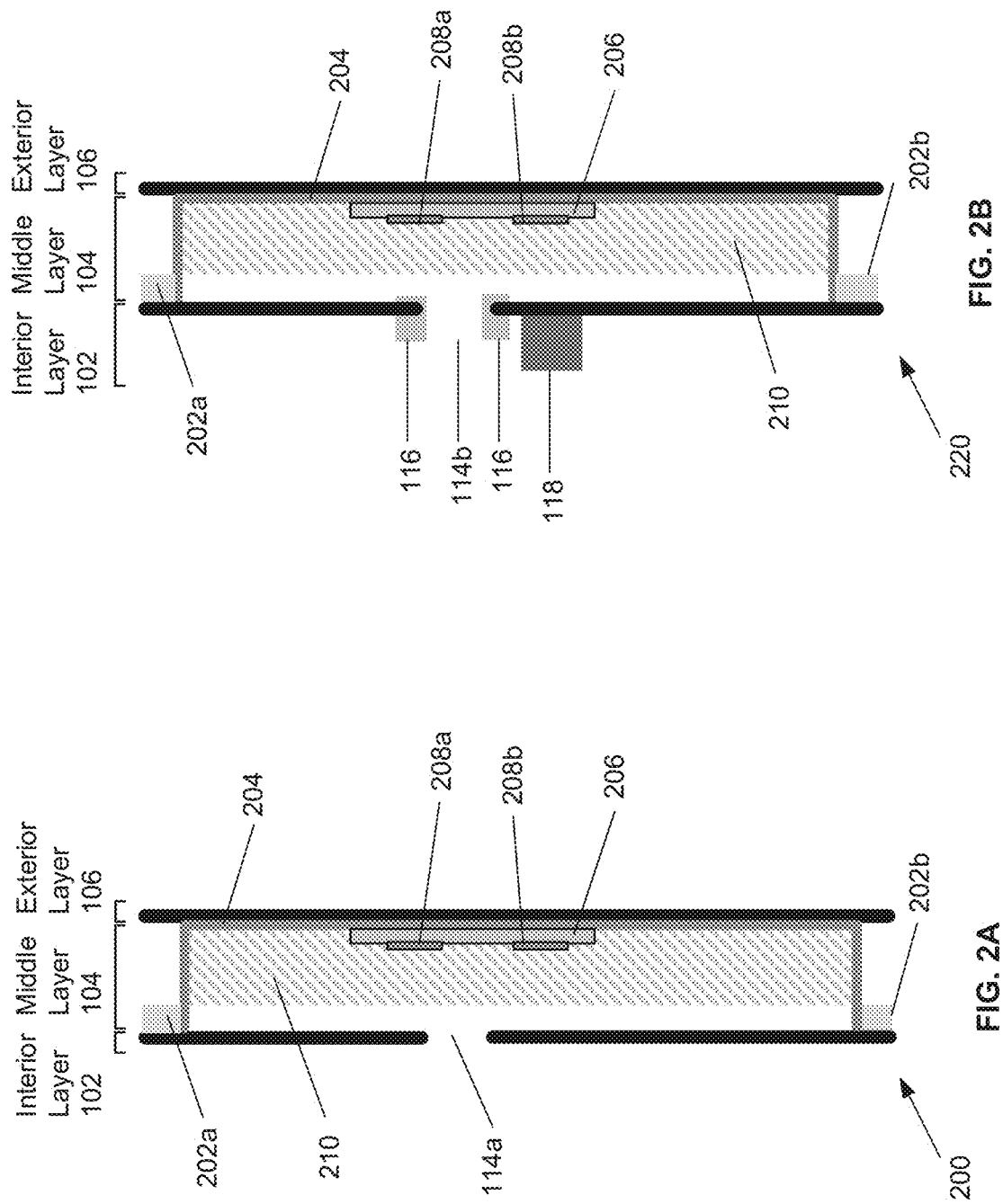

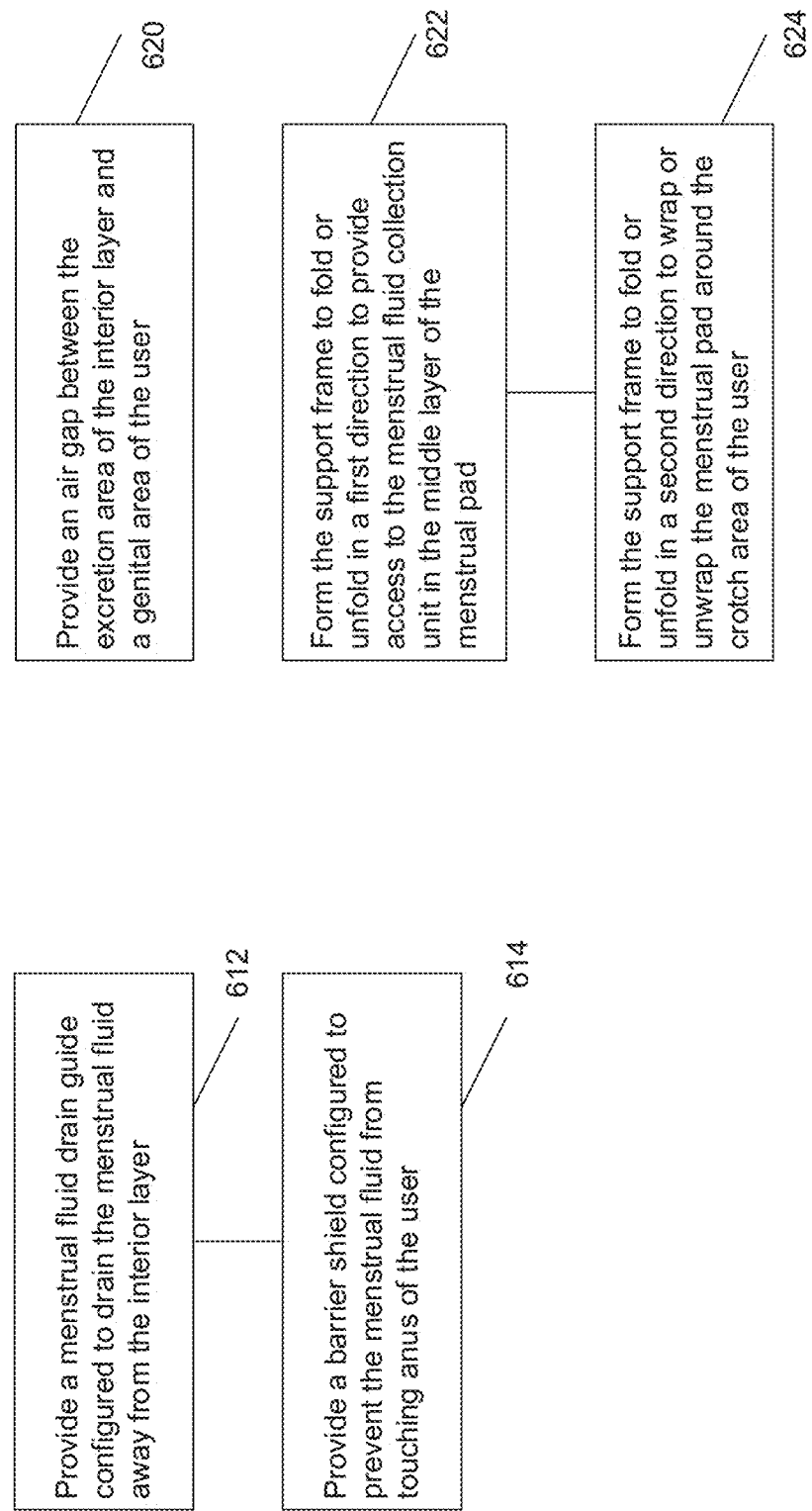

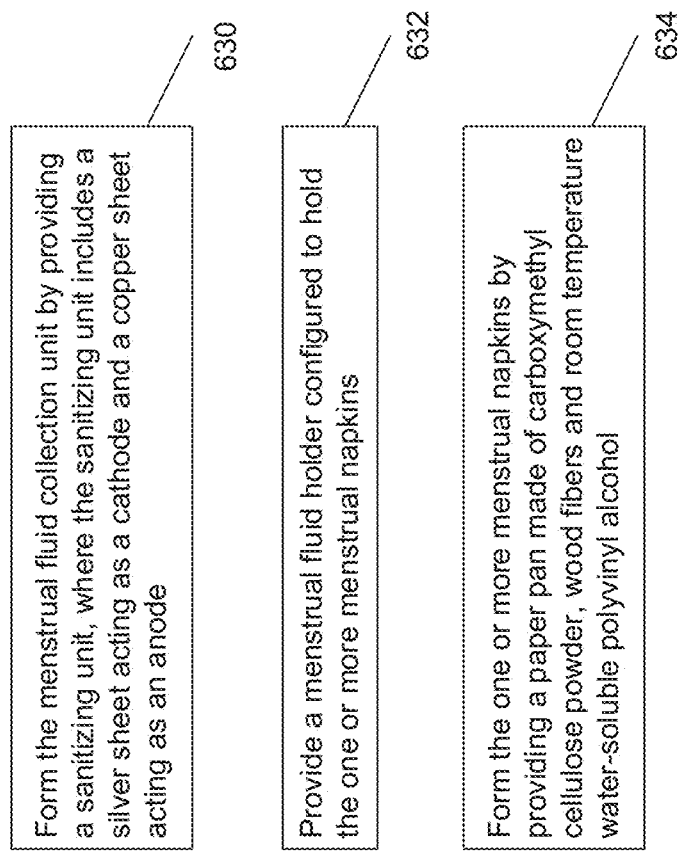

REUSABLE MENSTRUAL PAD

FIELD

The present invention relates to the field of menstrual hygiene materials. In particular, the present invention relates to apparatuses of a reusable menstrual pad and methods for manufacturing the same.

BACKGROUND

Conventional menstrual pads have been widely used. Although they possess moisture absorption properties, there are a number of drawbacks. First, after each use, the entire blood stained menstrual pad would be disposed of, creating a large amount of non-biodegradable waste materials. Second, even though the conventional menstrual pads may be able to absorb the moisture from the menstrual fluid, a blood stain menstrual pad may still be in direct contact with a user's genital. The blood stained menstrual pad may contain bacteria and thus cause infections. Therefore, there is a need for an environmentally-friendly reusable menstrual pad that can address the drawbacks of conventional menstrual pads.

SUMMARY

Apparatuses of reusable menstrual pad and methods for manufacturing the same are provided. In one embodiment, a menstrual pad includes an interior layer includes an excretion area, where the excretion area includes an opening configured to drain menstrual fluid of a user away from the interior layer; a middle layer configured to house a menstrual fluid collection unit, where the menstrual fluid collection unit is configured to sanitize the menstrual fluid drained from the interior layer and to store the sanitized menstrual fluid to one or more menstrual napkins in the middle layer; an exterior layer configured to conceal and prevent leakage from the middle layer of the menstrual pad; and a support frame configured to hold the interior layer, the middle layer and the exterior layer of the menstrual pad together.

In another embodiment, a method of manufacturing a menstrual pad includes forming an interior layer, where the interior layer includes an excretion area, and the excretion area includes an opening configured to drain menstrual fluid of a user away from the interior layer; forming a middle layer, where the middle layer is configured to house a menstrual fluid collection unit, and the menstrual fluid collection unit is configured to sanitize the menstrual fluid drained from the interior layer and to store the sanitized menstrual fluid to one or more menstrual napkins in the middle layer; forming an exterior layer, where the exterior layer is configured to conceal and prevent leakage from the middle layer of the menstrual pad; and forming a support frame, where the support frame is configured to hold the interior layer, the middle layer and the exterior layer of the menstrual pad together.

BRIEF DESCRIPTION OF THE DRAWINGS

The aforementioned features and advantages of the disclosure, as well as additional features and advantages thereof, will be more clearly understandable after reading detailed descriptions of embodiments of the disclosure in conjunction with the non-limiting and non-exhaustive aspects of following drawings. The drawings are shown for illustration purposes. They are not drawn to scale. Like numbers are used throughout the specification.

FIG. 1A illustrates a top view of an exemplary reusable menstrual pad according to aspects of the present disclosure.

FIG. 1B illustrates a top view of another exemplary reusable menstrual pad according to aspects of the present disclosure.

FIG. 2A illustrates a cross sectional view of the exemplary reusable menstrual pad of FIG. 1A according to aspects of the present disclosure.

FIG. 2B illustrates a cross sectional view of the exemplary reusable menstrual pad of FIG. 1B according to aspects of the present disclosure.

FIG. 6B illustrates an exemplary method of forming an interior layer of the reusable menstrual pad of FIG. 6A according to aspects of the present disclosure.

FIG. 6C illustrates an exemplary method of forming a support frame of the reusable menstrual pad of FIG. 6A according to aspects of the present disclosure.

FIG. 6D illustrates an exemplary method of forming a menstrual fluid collection unit of the reusable menstrual pad of FIG. 6A according to aspects of the present disclosure.

DESCRIPTION OF EMBODIMENTS

Figure 3B:
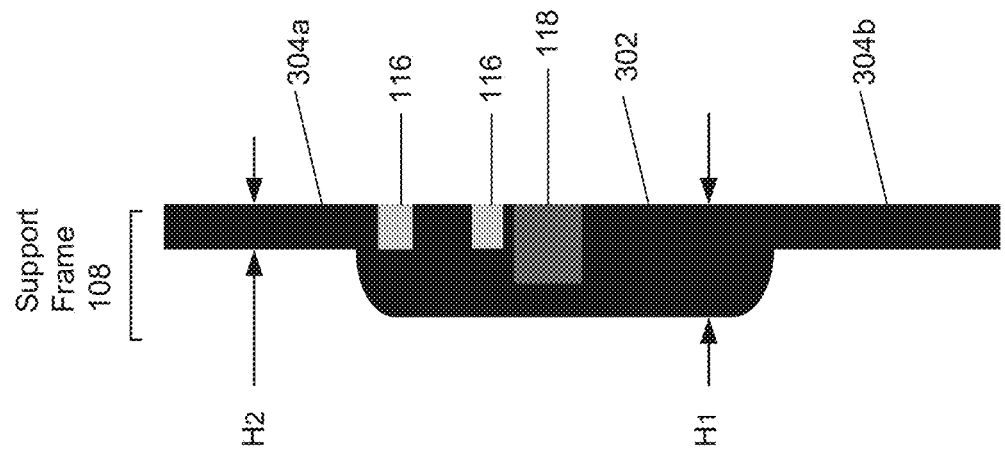
FIG. 3B illustrates a side view of the support frame of FIG. 1B according to aspects of the present disclosure.

Apparatuses of reusable menstrual pads and methods for manufacturing the same are provided. The following descriptions are presented to enable a person skilled in the art to make and use the disclosure. Descriptions of specific embodiments and applications are provided only as examples. Various modifications and combinations of the examples described herein will be readily apparent to those skilled in the art, and the general principles defined herein may be applied to other examples and applications without departing from the scope of the disclosure. Thus, the present disclosure is not intended to be limited to the examples described and shown, but is to be accorded the scope consistent with the principles and features disclosed herein. The word "exemplary" or "example" is used herein to mean "serving as an example, instance, or illustration." Any aspect or embodiment described herein as "exemplary" or as an "example" is not necessarily to be construed as preferred or advantageous over other aspects or embodiments.

FIG. 1A illustrates a top view of an exemplary reusable menstrual pad according to aspects of the present disclosure. In the example of FIG. 1A, a reusable menstrual pad 100 includes an interior layer 102 and a support frame, represented by lines 108. The interior layer 102 includes an excretion area, outlined with the dash lines 112a. The excretion area includes an opening 114a configured to drain excretions of a user away from the interior layer 102. The interior layer 102 is made of a hydrophobic material configured to repel the excretions of the user from the opening 114a to a middle layer of the exemplary reusable menstrual pad. The middle layer 104 and exterior layer 106 (not visible from the top view) are underneath the interior layer 102 of the reusable menstrual pad 100.

According to aspects of the present disclosure, the interior layer 102 can be made of a breathable, stretchable polytetrafluoroethylene treated cotton-spandex waterproof fabric sheet or polytetrafluoroethylene treated nylon-spandex waterproof fabric sheet. In another approach, the interior layer 102 can be made of breathable and water repellent waxed cotton fabric, polyurethane coated microfiber or silicone coated cotton-lycra fabric. The interior layer 102 is attached to the support frame 108. The upper surface of the interior layer is configured to closely contact with the skin of a user to avoid skin rashes and stains from menstrual excretions. The lower surface, also referred to as the excretion area, of the interior layer is configured to adhere with a menstrual fluid collection unit, which is to be further described below.

According to aspects of the present disclosure, the support frame 108 is configured to hold the interior layer 102, the middle layer 104 and the exterior layer 106 of the menstrual pad together. The support frame is made of hydrophobic polydimethylsiloxane rubber or thermoplastic elastomers, and is configured to wrap around the crotch area of the user to prevent leakage.

FIG. 1B illustrates a top view of another exemplary reusable menstrual pad according to aspects of the present disclosure. Some of the components of the reusable menstrual pad 120 are the same as the components shown in FIG. 1A, such as the interior layer 102, the support frame 108, and the excretion area 112b. The description of similar components are not repeated here. In the example of FIG. 1B, the excretion area of the interior layer 102 includes a menstrual fluid drain guide 116, represented by an oval ring, is configured to drain menstrual fluid of a user away from the interior layer 102. The menstrual fluid drain guide surrounds the opening 114b. The excretion area further includes barrier shield 118, configured to prevent menstrual fluid from reaching anus of the user.

According to aspects of the present disclosure, the interior layer includes a menstrual drain opening (also referred to as the opening for short) in the genital area. The menstrual drain opening is configured to drain the menstrual fluid of the user to the menstrual fluid collection unit through the opening. The menstrual fluid drain guide has a top surface adhered around the menstrual drain opening on the interior layer configured to prevent menstrual fluid to stain the front microfiber pad in the abdomen area and the rear microfiber pad in the buttocks area.

In some implementations, the menstrual fluid drain guide 116 has a top surface made of polydimethylsiloxane rubber with a dimensional of 2 cm to 5 cm in width and 7 to 10 cm in length, configured to drain menstrual fluid from the genital and move downward into the menstrual fluid collection unit.

FIG. 2A illustrates a cross sectional view of the exemplary reusable menstrual pad of FIG. 1A according to aspects of the present disclosure. It shows components of the interior layer 102, the middle layer 104 and the exterior layer 106 of the reusable menstrual pad in a cross sectional view. As shown in FIG. 2A, the middle layer 104 is configured to house a menstrual fluid collection unit, which is configured to sanitize the menstrual fluid drained from the interior layer 102 and to store the sanitized menstrual fluid to one or more menstrual napkins in the middle layer 104. The middle layer 104 further includes one or more menstrual napkins, represented by 210, configured to extract moisture from the menstrual fluid captured by the menstrual fluid collection unit.

According to aspects of the present disclosure, the middle layer 104 is configured to hold the menstrual fluid collection unit between the interior layer 102 and the exterior layer 106. The menstrual fluid collection unit includes a menstrual fluid holder 204 and a menstrual fluid sanitizing unit. The menstrual fluid sanitizing unit, represented by 206 as well as 208a and 208b, configured to sanitize menstrual fluid collected in the menstrual fluid holder 204.

In some implementations, the middle layer 104 includes a front microfiber pad 202a, a rear microfiber pad 202b, and optionally a front air drying pouch and a rear air drying pouch (not shown) for keeping dryness in the abdomen, genital and buttocks areas. The front microfiber pad is adhered on the interior layer in the abdomen area and the rear microfiber pad is adhered on the interior layer in the buttocks area, where both of the front and rear microfiber pads are shielded by the menstrual fluid holder to avoiding contact with the menstrual fluid, so that the front and rear microfiber pads can be cleaned and reused as they have not been in contact with blood stains. The front microfiber pad 202a and the rear microfiber pad 202b can be made of a hydrophilic wicking material such as microfiber non-woven fabric with a dimension of 6 cm×12 cm×3 mm. The upper surface of the front microfiber pads is adhered on the inner surface of the interior layer in the abdomen portion. The rear microfiber pads are adhered on the inner surface of the interior layer in the buttocks portion. The front air drying pouch is adhered on the inner layer of the exterior layer in the abdomen portion. The rear air drying pouch is adhered on the inner layer of the exterior layer in the buttocks portion configured to when the interior layer and the exterior are folded together the front air drying pouch may contact with the front microfiber pad and the rear air drying pouch may contact with the rear microfiber pad for keeping dryness in the abdomen and buttocks area, besides when the interior layer is horizontal unfolded from the exterior layer to open the menstrual pad configured to clean the reusable components of the menstrual pad to change the wetted air dry pouch and flush the menstrual napkin.

According to aspects of the present disclosure, the exterior layer 106 is configured to conceal and prevent leakage from the middle layer 104 of the reusable menstrual pad. The exterior layer 106 is made of a breathable material configured to allow moisture from the middle layer to escape the menstrual pad. The exterior layer is made of stretchable and breathable polytetrafluoroethylene waterproof film. In another approach, the exterior layer 106 is made of stretchable and breathable silicone coated lycra stretch fabric, polyurethane coated polyester spandex or polytetrafluoroethylene waterproof material configured to allow moisture from the middle layer to escape the menstrual pad. The front air drying pouch is detachable adhered on the inner surface of the exterior layer in the abdomen portion and a rear air drying pouch is detachable adhered on the inner surface of the exterior layer in the buttocks portion configured to serve as a protective cover sheet of the menstrual pad.

FIG. 2B illustrates a cross sectional view of the exemplary reusable menstrual pad of FIG. 1B according to aspects of the present disclosure. Similar to FIG. 2A, it shows components of the interior layer 102, the middle layer 104 and the exterior layer 106 of the reusable menstrual pad in a cross sectional view. Some of the components shown in FIG. 2B are the same as the components shown in FIG. 2A, and the description of such components are not repeated here.

In the example shown in FIG. 2B, the interior layer 102 includes a menstrual fluid drain guide 116 configured to drain menstrual fluid of a user away from the interior layer 102. The menstrual fluid drain guide surrounds the opening 114b. The interior layer 102 further includes barrier shield 118, configured to prevent menstrual fluid from reaching anus of the user. In the middle layer 104, the location of the menstrual fluid collection unit may be different from the location shown in FIG. 2A. The size of menstrual napkin(s) 210 may be adjusted accordingly based on the location of the menstrual fluid collection unit.

In some implementations, the middle layer includes a front microfiber pad 202a being adhered on the interior layer around the upper rim of the menstrual fluid holder 204 and a rear microfiber pad 202b being adhered on the interior layer around the lower rim of the menstrual fluid holder 204. The interior layer is made of a breathable, stretchable polytetrafluoroethylene treated cotton-spandex waterproof fabric sheet or polytetrafluoroethylene treated nylon-spandex waterproof fabric sheet. The left end side of the interior layer is bonded on the outer edge of the left side of the support frame and the right end side of the interior layer is detachable adhered on the outer edge of the right side of the support frame to form a flip-up interior layer configured to enclose the menstrual fluid collection unit to collect, absorb and avoid leakage of the menstrual discharges.

The menstrual fluid collection unit may further comprise a menstrual fluid holder, a sanitizing unit and one or more menstrual napkins. In some implementations, the menstrual fluid holder can be made of polydimethylsiloxane rubber which has a dimension of 10 cm to 15 cm in length, 3.5 cm to 5.5 cm in width and the thickness is 0.8 cm to 1.5 cm configured to have a capacity about 28 ml to 81 ml to collect and absorb menstrual fluid. The dimension of the menstrual fluid drain guide can be 7 cm to 10 cm in length, 2 cm to 5 cm in width and the thickness can be 3 mm configured to fit the significant variations in user's genital size. The menstrual fluid drain guide is adhered on the outer surface of the interior layer around the menstrual drain opening. The menstrual fluid drain guide may snug fitting the outer portion of the female genital configured to drain the menstrual fluid from the genital into the menstrual fluid holder and prevent menstrual fluid from staining the skin of the user.

The one or more removable menstrual napkins can be adhered on the inner surface of the menstrual fluid holder 204. The one or more menstrual napkins are configured to accelerate menstrual fluid absorption by spreading and transferring menstrual fluid evenly to the one or more menstrual napkins.

The sanitizing unit includes two pieces of reusable sanitizing sheets 208a and 208b made of ionizing metallic fabric. The ionizing metallic fabric includes one or more of copper fiber, silver fiber, zinc fiber or copper silver blend nonwoven fabric. In one approach, the sanitizing sheets 208a such as a silver sheet which is served as a cathode and a copper sheet 208b which is served as an anode, both 208a and 208b can be adhered on the inner surface of the menstrual fluid holder, which may be near the menstrual fluid drainage area. An electrically conductive adhesive film, shown as 206 such as electrically conductive epoxy coated polydimethylsiloxane rubber or polyethylene pressure sensitive adhesive can be adhered on the outer lower portion of the sanitizing sheets 208a and 208b configured to electrical connect and mechanical bond the sanitizing sheets 208a and 208b to the inner surface of the menstrual fluid holder to contact with the menstrual napkin. When menstrual fluids drop onto the menstrual napkin then the sanitizing sheets may be wetted by the menstrual fluid which may include sodium ions and potassium ions that serve as an electrolyte. As a result, the silver cathode, the copper anode and the menstrual fluid electrolyte can initiate an electrochemical corrosion reaction that facilitates the copper to oxidize into antibacterial copper ions, which in turn sanitize the menstrual fluid.

Figure 3A:
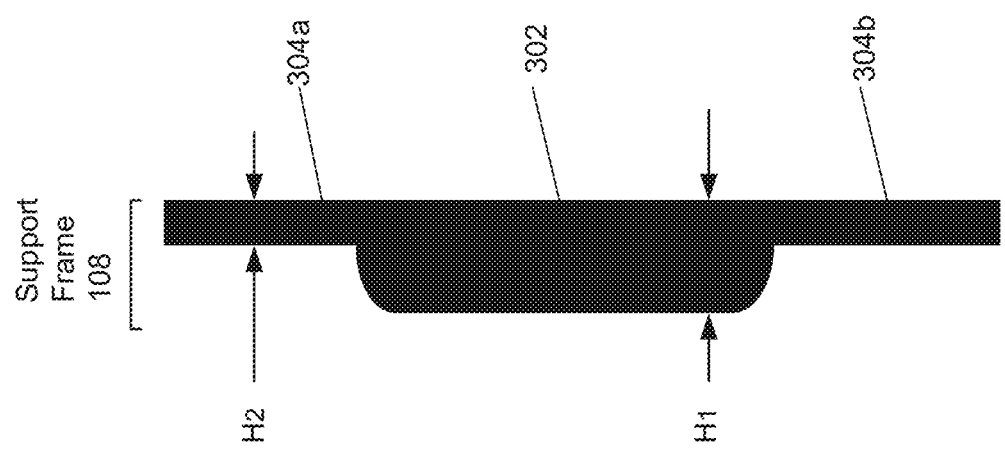
FIG. 3A illustrates a side view of the support frame of FIG. 1A according to aspects of the present disclosure.

FIG. 3A illustrates a side view of the support frame of FIG. 1A according to aspects of the present disclosure. As shown in FIG. 3A, the support frame 108 may have different heights in the excretion section and non-excretion section. The support frame in the excretion section may have a height of $H_1$. The height of $H_1$ depends on different sizes for different users, which may have a range of 1.2 to 1.5 centimeters, configured to ensure the menstrual fluid collection unit has enough volume to collect menstrual fluid. The support frame in the non-excretion section has a height of $H_2$. The height of $H_2$ depends on different sizes for different users, which may have a range of 0.3 to 0.5 centimeters.

According to aspects of the present disclosure, the increased height of the support frame in the excretion area is designed to seal the menstrual pad to the crotch area of the user and to provide an air gap between the excretion area of the interior layer of the menstrual pad and a genital area of the user. The air gap reduces or prevents blood stains from touching the skin of the user. The height of the support frame in the non-excretion section is designed to have a lower height than the excretion area to minimize bulging, which allows a close snug to the skin of the user in the lower abdominal and rear areas of the menstrual pad.

According to aspects of the present disclosure, the support frame is configured to fold or unfold in a first direction to provide access to the menstrual fluid collection unit in the middle layer of the menstrual pad; and where the support frame may also be configured to fold or unfold in a second direction to wrap or unwrap the menstrual pad around the crotch area of the user.

In some implementations, the support frame can be made of hydrophobic polydimethylsiloxane rubber or thermoplastic elastomers sheet which is adhered on the inner surface of the exterior layer for enclosing the front abdomen, crotch and buttocks areas configured to seal the menstrual pad to a crotch area of the user and to provide a space for the menstrual fluid collection unit and a genital of the user. As shown in FIG. 3A, the support frame is adhered on the exterior layer which has three sections. A first section 302 of the support frame is located around the genital area of the user. A first part of the menstrual fluid holder may be bonded with the support frame which is located at 2 cm above the genital. A second part of the menstrual fluid holder may be bonded with the support frame which is located near the tailbone area. A third part of the menstrual fluid holder may be bonded to the support frame and the exterior layer. A second section 304a of the support frame may be located at a front portion of the crotch area configured to hold the front microfiber pad that touches the interior layer of an abdominal area of the user. A third section 304*b* of the support frame may be located at a back portion of the crotch area that is configured to hold the rear microfiber pad that touches the interior layer of a rear area of the user.

FIG. 3B illustrates a side view of the support frame of FIG. 1B according to aspects of the present disclosure. Similar to FIG. 3A, some of the components shown in FIG. 3B are the same as the components shown in FIG. 3A, and the description of such components are not repeated here.

In some implementations, the support frame can be made of 1 cm wide elastic material such as polydimethylsiloxane rubber, where the thickness of the support frame can be different in the three sections, it is 3 mm to 6 mm thick in the anterior abdomen section and buttocks section, and 1 cm to 1.2 cm in thickness in the excretion section configured to make thin menstrual pad but has enough volume to collect menstrual fluid and provide 12 hours leak-free protection for heavier flows. In the anus area, a horizontal barrier shield made of elastic material such as polysiloxane with 4 cm to 6 cm in length, 3 cm to 4 cm in width and 2 mm in thickness, which can be configured to prevent the menstrual fluid from reaching anus.

Figure 3C:
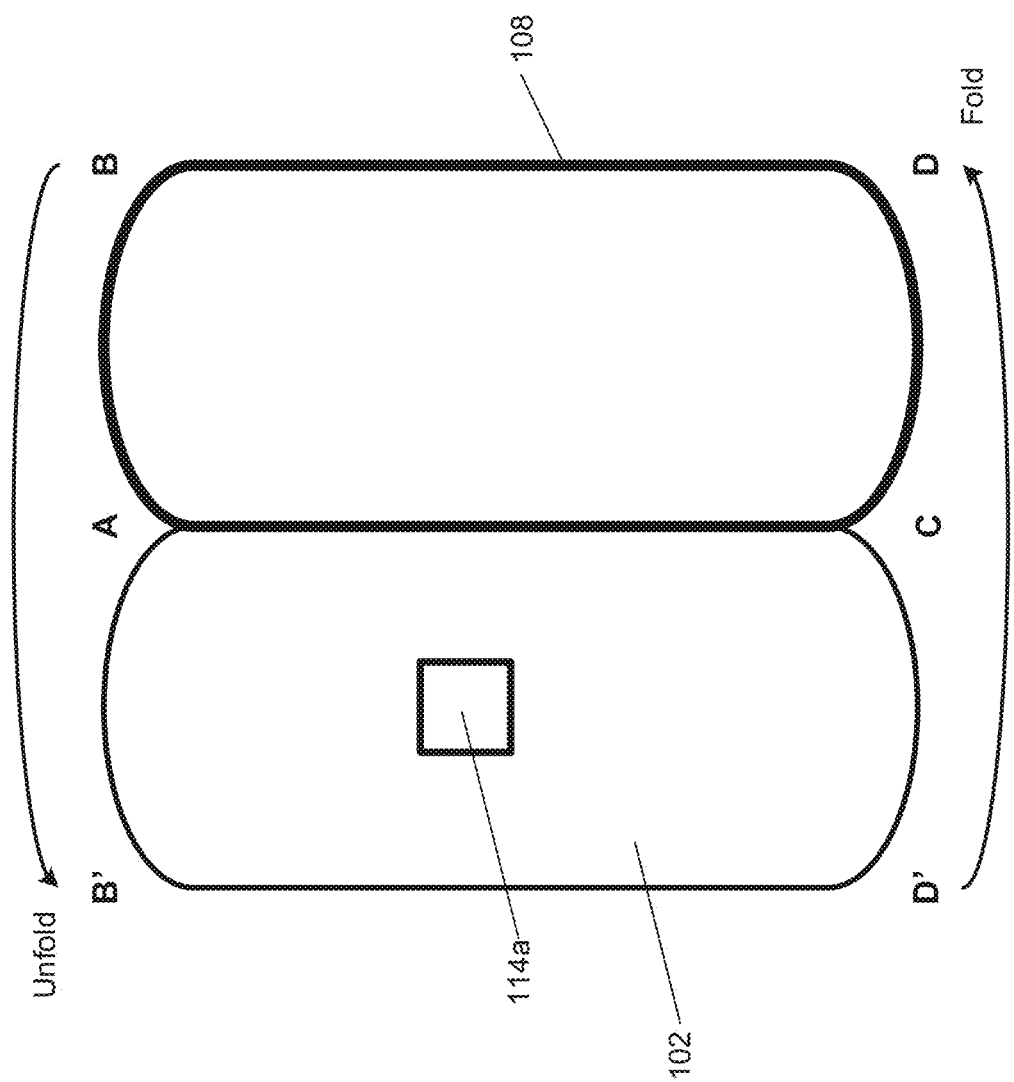
FIG. 3C illustrates an exemplary implementation of fold and unfold operations of the exemplary reusable menstrual pad of FIG. 1A according to aspects of the present disclosure.

FIG. 3C illustrates an exemplary implementation of fold and unfold operations of the exemplary reusable menstrual pad of FIG. 1A according to aspects of the present disclosure. As shown in FIG. 3C, the support frame, represented by connected points A, B, C, and D, may be folded and unfolded to provide access to the middle layer of the reusable menstrual pad for cleaning or changing the menstrual napkins. In this exemplary implementation, the support frame on the right hand side of the menstrual pad may be configured to be detachable along the line BD. In the unfold form, the middle layer 104, the exterior layer 106 and the support frame remain on the right hand side, shown as ABCD (top view), while the interior layer 102 is moved to the left hand side of FIG. 3C, shown as B'ACD'. In the unfold form, menstrual napkins stored in the middle layer of the reusable menstrual pad (not shown) may be changed; the menstrual fluid collection unit and other components of the middle layer may be cleaned. After accessing the middle layer, the menstrual pad may be folded by attaching the interior layer 102 back to the support frame 108, i.e. line B'D' is folded back to line BD.

Note the directions of the fold and unfold operations in FIG. 3C are shown for illustration purposes. In other embodiments, the support frame 108 may be configured to be detachable along the line AB (not shown). In yet other embodiments, the support frame 108 may be configured to be detachable along the line AC or CD (not shown). According to aspects of the present disclosure, the folding and unfolding mechanism may be implemented by various means, for example using magnetic strips, adhesive strips, Velcro strips, and etc.

Figure 4B:
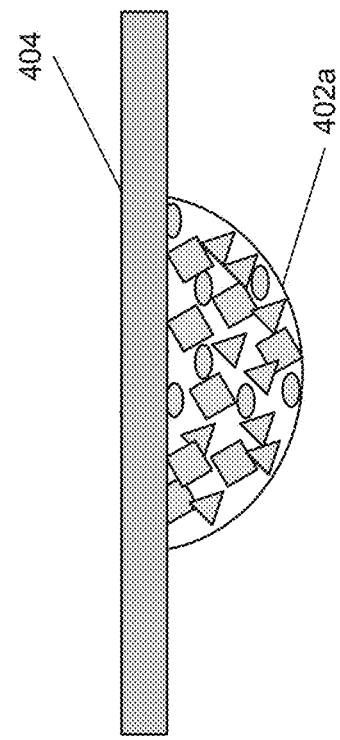
FIG. 4B illustrates an exemplary implementation of a collection cup of the menstrual napkin of FIG. 4A according to aspects of the present disclosure.
Figure 4A:
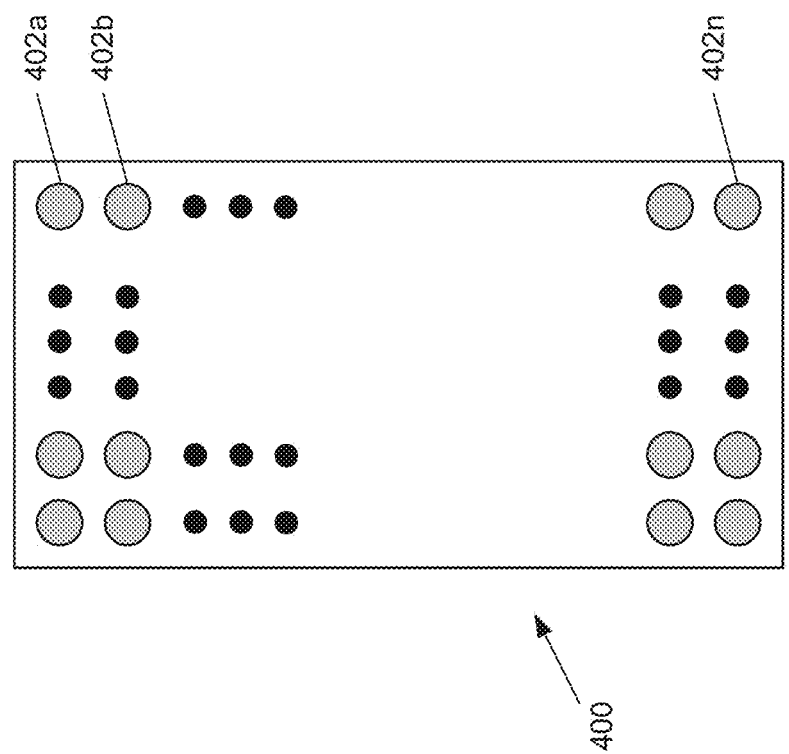
FIG. 4A illustrates an exemplary implementation of a menstrual napkin according to aspects of the present disclosure.

FIG. 4A illustrates an exemplary implementation of a menstrual napkin according to aspects of the present disclosure. FIG. 4B illustrates an exemplary implementation of a collection cup of the menstrual napkin of FIG. 4A according to aspects of the present disclosure. In this exemplary implementation, a menstrual napkin 400 may include a group of collection cups (represented by 402*a*, 402*b* . . . 402*n*, etc.) connected with a carboxymethyl cellulose (CMC) paper sheet 404. Each cup, for example 402*a*, in the group of collection cups can be configured to hold biodegradable superabsorbent polymer particles and toilet paper scraps for absorbing menstrual fluid from the user.

According to aspects of the present disclosure, a used menstrual napkin is flushable in a toilet. Based on the size of the user and other application criteria, various sizes of menstrual napkins may be designed. In one implementation, a menstrual napkin having a rectangular shape of approximately 2.5 cm to 3 cm in width and 10 cm to 14 cm in length may be used to fit the drainage of a toilet. In some embodiments, a reusable menstrual pad may be designed to hold multiple menstrual napkins for situations where it is desirable to prolong the period of changing the menstrual napkins.

The menstrual napkin is designed with the following features, including but not limited to: 1) use a flushable, dispersible and biodegradable CMC paper; 2) supported by the menstrual fluid holder and the support frame to provide space for the superabsorbent polymer particles to undergo free swelling process in order to maximize menstrual fluid absorption capacity; 3) provide a uniform distribution of 2 grams to 3 grams biodegradable super absorbent polymer particles in the group of collection cups of the menstrual napkin; and 4) enable a used menstrual napkin to disintegrate in toilet water.

According to aspects of the present disclosure, the menstrual napkin uses collection cups to achieve desirable swelling rate and swelling capacity. One advantage of the disclosed menstrual napkin is that it can be disintegrated in water, allowing used menstrual napkin to be flushed in a toilet. In some implementations, based on the size and intended duration of use of the menstrual pad, the main structure of a menstrual napkin may include 6 to 20 or more collection cups as the SAP particles holder, for example in 6×1, 6×2, 10×1 and 10×2 configurations. In the example of the 6×1 configuration, the menstrual napkin may have a dimension of 14 cm×2.5 cm×1.2 cm, where the 6 collection cups may be made by mixing appropriate proportions of CMC powder, wood fibers and room temperature water-soluble polyvinyl alcohol into pulp and hot-press pulp into a menstrual napkin with 6 collection cups.

In some implementations, depending on the size and intended duration of use of the menstrual pad, each cup may have a dimension 2 cm×2.2 cm×1 cm with a volume of about 4.4 milliliter (ml) and with a total volume of about 26.4 ml and a thin mesh shape flushable CMC paper sheet as the cover of the cup.

Each cup can be filled with a mixture of dry two ply toilet paper scraps and about 200 mg to 400 mg of biodegradable superabsorbent polymer particles, then put another 3 mm thick two ply toilet paper sheet on the top of the mixture of two ply toilet paper scraps and biodegradable superabsorbent polymer particles and then put a 2 mm thick flushable CMC paper cover on the top of the cups, and then the water-soluble pressure-sensitive adhesive is used to seal the cups with the flushable CMC paper cover to form a 14 cm×2.5 cm×1.2 cm menstrual napkin. This method of sandwiching the biodegradable superabsorbent polymer particles between the two ply toilet paper strips is to use toilet paper absorb menstrual fluid to provide the biodegradable superabsorbent particles having time to absorb menstrual fluid and dry out the toilet paper for the next round of menstrual fluid absorption. The collection cups are configured to provide room required for the expansion of wetted biodegradable superabsorbent polymer particles. The biodegradable superabsorbent polymer particles in the menstrual napkin are under free swelling to have an optimal menstrual fluid absorption capacity, which in turn keeps the genital area drying and prevents rashes to the skin of the user. In some other implementations, several of the menstrual napkins may be used together according to the actual menstrual fluid absorption needs or desired duration between menstrual pad changes.

For example one 6×2 configuration menstrual napkin may include two parallel pieces of 14 cm×2.5 cm×1.2 cm menstrual napkins, which may be formed on the top surface of a room temperature water-soluble polyvinyl alcohol film, then a water soluble polyvinyl alcohol pressure sensitive adhesive may be used to bond two parallel pieces of 14 cm×2.5 cm×1.2 cm menstrual napkins together to form a 14 cm×5 cm×1.2 cm menstrual napkin.

In some other implementations, the structure of the menstrual napkin includes a flushable CMC paper shallow pan. The flushable CMC paper shallow pan is made by mixing appropriate proportions of carboxymethyl cellulose powder (CMC), wood fibers and room temperature water-soluble polyvinyl alcohol into pulp and hot-press pulp into a flushable CMC paper shallow pan with a thickness of 0.6 cm to 1 cm. The inside space of the paper shallow pan is divided into 6 to 12 collection cups, such a 6×1 and 6×2 configurations configured to uniformly distribute the biodegradable super absorbent polymer particles in each collection cup. A mixture of 2 mm to 3 mm flushable 2 ply toilet paper strips and the biodegradable SAP particles may fulfill the biodegradable SAP particles collection cups of the flushable CMC paper shallow pan. Each collection cup may contain 200 mg to 400 mg of the biodegradable SAP particles. Then, using the water-soluble pressure-sensitive adhesive to seal the SAP particles filled flushable CMC paper shallow pan with the mesh shape CMC paper lid to form a rectangular menstrual napkin. An exemplary menstrual napkin may have a dimension of 1.2 centimeter in thickness, 14 centimeter in length and 2.5 centimeter in width, which may be configured to hold 1.2 g the biodegradable SAP particles and has a volume about 24 cubic millimeters, providing a thin menstrual pad but with maximum level of protection. The function of the flushable CMC paper strips is to hold the menstrual fluid, giving the biodegradable superabsorbent polymer particles sufficient time to absorb the menstrual fluid. The function of the flushable CMC paper shallow pan is to provide enough space required for the expansion of wetted biodegradable superabsorbent polymer particles. So the biodegradable superabsorbent polymer particles in the disclosed menstrual napkin can function under free swelling to provide a maximum fluid absorption capacity for keeping the genital dry. Note that the menstrual napkin can be removed and replaced. A used menstrual napkin can be disposed of into the toilet, which can be safely flushed down the sewer pipes.

Figure 5B:
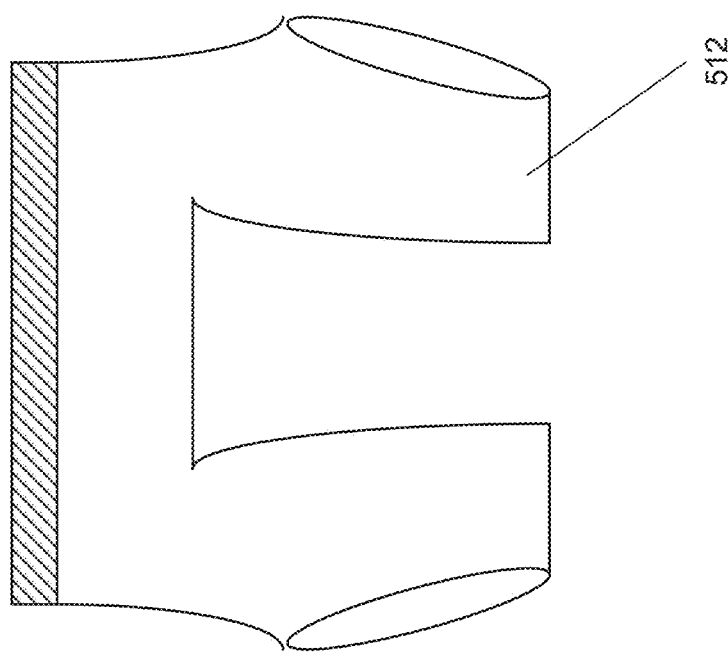
FIG. 5B illustrates an exemplary open crotch underwear to be used with the reusable menstrual pad of FIG. 5A according to aspects of the present disclosure.
Figure 5A:
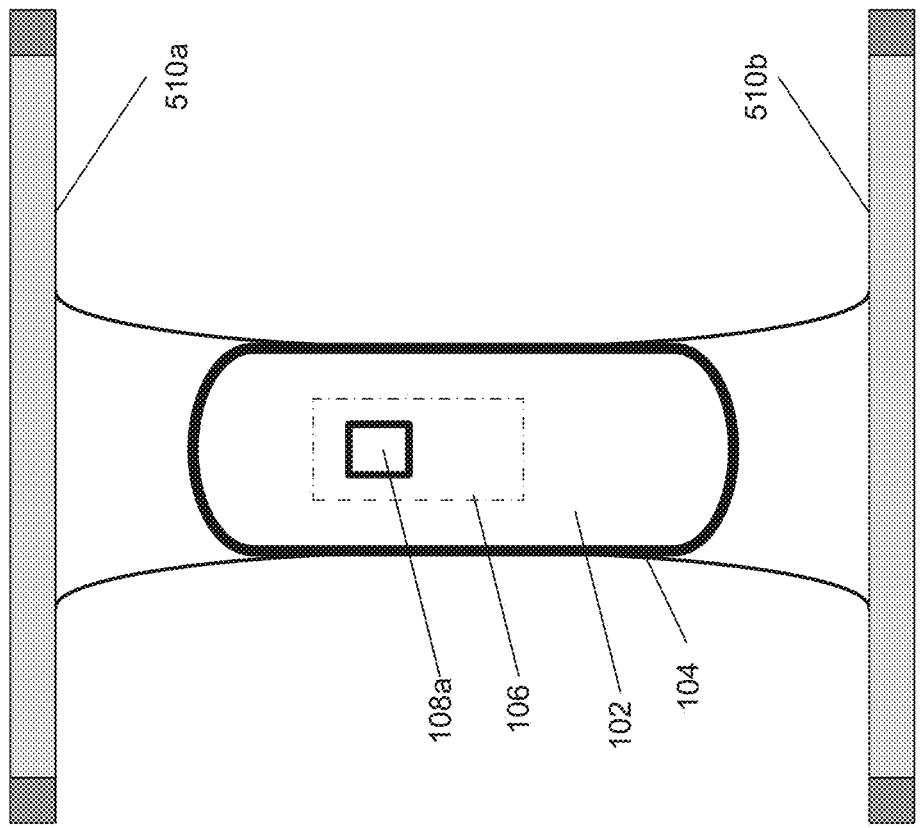
FIG. 5A illustrates an exemplary usage of a reusable menstrual pad as a wearable according to aspects of the present disclosure.

FIG. 5A illustrates an exemplary usage of a reusable menstrual pad as a wearable according to aspects of the present disclosure. As shown in FIG. 5A, a reusable menstrual pad 100 may be configured to work with a strapping mechanism, represented by 510a and 510b, configured to strap the reusable menstrual pad to the body of a user.

In some exemplary implementations, the menstrual pad can be adapted to be secured to the user with a wide elastic front waist belt, a wide elastic back waist belt, and two elastic straps which are bonded on the outer surface of the left side and right side of the exterior layer configured to press the interior layer, the menstrual fluid drain guide, the menstrual fluid holder, and the horizontal barrier shield to contact with the user's skins around the crotch portion configured to fix the menstrual fluid collection units in proper position to collect menstrual fluid and prevent menstrual fluid leak from the menstrual pad.

The lower surface of the front waist part of the exterior layer is bonded with a wide elastic belt which has self-adhesive tapes on the left and right sides. The lower surface of the back waist part of the exterior layer is also bonded with a wide elastic belt which has self-adhesive types on the left and right sides. Both of the opposite sides of the self-adhesive tapes of the front waist part and the back waist part can be folded or unfolded in the vertical direction configured to wrap or unwrap the menstrual pad around the crotch area of the user, as described above in association with FIG. 3C. The flip up interior layer can be folded or unfolded in a horizontal direction and is further configured to provide access to the menstrual fluid collection unit in the middle layer of the menstrual pad. Note that when the menstrual pad is fixed on the waistband portion of the open crotch sanitary pants, the exterior layer may press the interior layer against the crotch area of the user, configured to fix the menstrual fluid drain guide, the menstrual fluid holder in place.

FIG. 5B illustrates an exemplary open crotch underwear to be used with the reusable menstrual pad of FIG. 5A according to aspects of the present disclosure. As shown in FIG. 5B, a reusable menstrual pad may be configured to work with a pair of open crotch pants 512, allowing users to manage the periods conveniently, hygienically, comfortably, economically, and at the same time in an environmentally friendly manner.

In some exemplary implementations, the reusable open crotch pants with an opening to expose the genitals for vaginal discharge. The reusable open crotch pants are designed with a two-layer structure. A base layer can be made of soft material such as cotton, viscose and microfiber nonwoven fabric, and an outer layer can be made of a stretchable, breathable waterproof material such as polyurethane coated polyester spandex or tetrafluoroethylene treated polyester-viscose or polyester-cotton non-woven fabric, configured to provide barriers for preventing menstrual fluid to permeate into the open crotch pants. One advantage is that there is no need to take off the open crotch pants when sitting on the toilet seat configured to prevent soil water on the dirty toilet from reaching the user's skin.

Figure 6A:
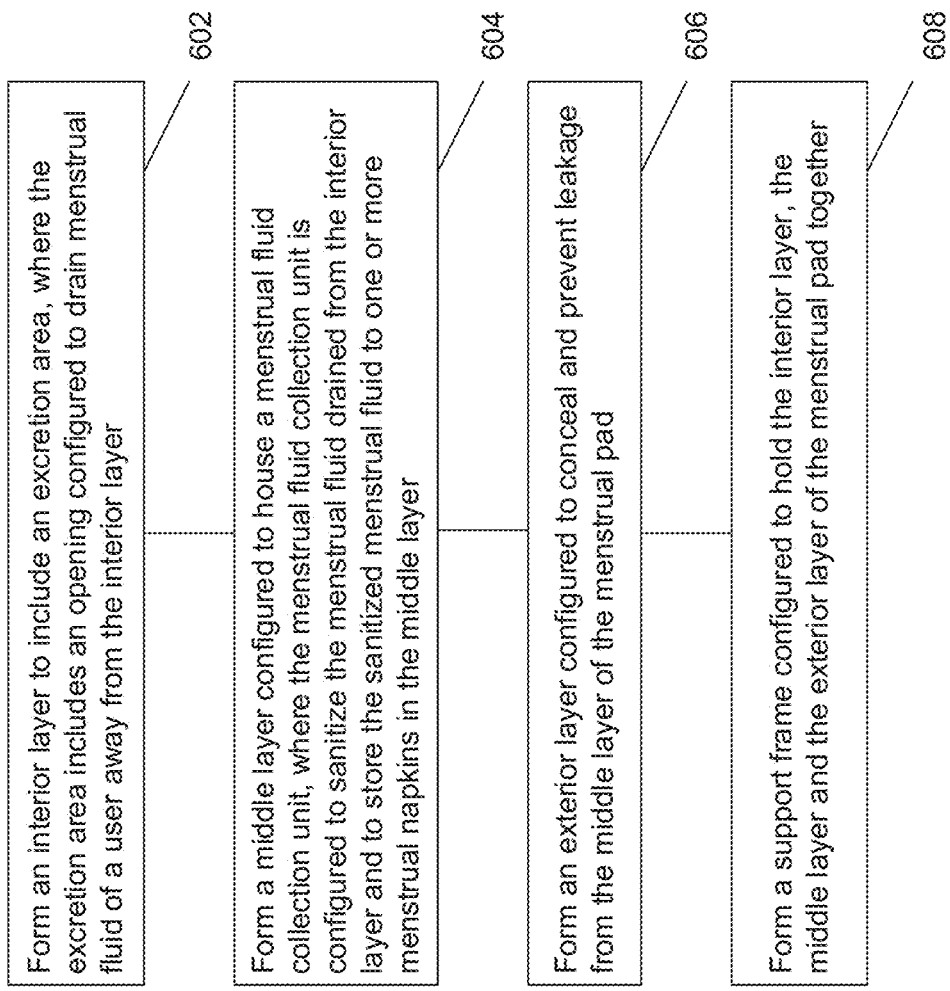
FIG. 6A illustrates an exemplary method of manufacturing a reusable menstrual pad according to aspects of the present disclosure.

FIG. 6A illustrates an exemplary method of manufacturing a reusable menstrual pad according to aspects of the present disclosure. In the example shown in FIG. 6A, in block 602, the method forms an interior layer to include an excretion area, where the excretion area includes an opening configured to drain menstrual fluid of a user away from the interior layer. In block 604, the method forms a middle layer configured to house a menstrual fluid collection unit, where the menstrual fluid collection unit is configured to sanitize the menstrual fluid drained from the interior layer and to store the sanitized menstrual fluid to one or more menstrual napkins in the middle layer. In block 606, the method forms an exterior layer configured to conceal and prevent leakage from the middle layer of the menstrual pad. In block 608, the method forms a support frame configured to hold the interior layer, the middle layer and the exterior layer of the menstrual pad together.

According to aspects of the present disclosure, the exterior layer of the menstrual pad may be formed using a breathable material configured to allow moisture from the middle layer to escape the menstrual pad, and the reusable menstrual pad may be configured to be used with an open crotch underwear or to be used with a regular underwear.

FIG. 6B illustrates an exemplary method of forming an interior layer of the reusable menstrual pad of FIG. 6A according to aspects of the present disclosure. As shown in FIG. 6B, in block 612, the method provides a menstrual fluid drain guide configured to drain the menstrual fluid away from the interior layer. In block 614, the method provides a barrier shield configured to prevent the menstrual fluid from touching anus of the user. According to aspects of the present disclosure, the interior layer is formed by using a hydrophobic material configured to repel the menstrual fluid of the user to the middle layer through the opening.

FIG. 6C illustrates an exemplary method of forming a support frame of the reusable menstrual pad of FIG. 6A according to aspects of the present disclosure. In the example shown in FIG. 6C, in block 620, the method provides an air gap between the excretion area of the interior layer and a genital area of the user. According to aspects of the present disclosure, the support frame is made of polydimethylsiloxane rubber or thermoplastic elastomers, and is configured to wrap around the crotch area of the user to prevent leakage. In block 622, the method forming the support frame to fold or unfold in a first direction to provide access to the menstrual fluid collection unit in the middle layer of the menstrual pad. In block 624, the method forms the support frame to fold or unfold in a second direction to wrap or unwrap the menstrual pad around the crotch area of the user.

FIG. 6D illustrates an exemplary method of forming a menstrual fluid collection unit of the reusable menstrual pad of FIG. 6A according to aspects of the present disclosure. In the exemplary method of FIG. 6D, in block 630, the method forms the menstrual fluid collection unit by providing a sanitizing unit, where the sanitizing unit includes a silver sheet acting as a cathode and a copper sheet acting as an anode. According to aspects of the present disclosure, the menstrual fluid in the menstrual fluid collection unit serves as an electrolyte to initiate an electrochemical corrosion reaction between the anode and the cathode, causing oxidize copper into antibacterial copper ions that sanitize the menstrual fluid. In block 632, the method provides a menstrual fluid holder configured to hold the one or more menstrual napkins, where the menstrual fluid holder is made of a hydrophobic material and is configured to prevent menstrual fluid leakage. In block 634, the method forms the one or more menstrual napkins by providing a paper pan made of carboxymethyl cellulose powder, wood fibers and room temperature water-soluble polyvinyl alcohol, where the paper pan includes a plurality of collection cups configured to hold biodegradable superabsorbent polymer particles, and a used menstrual napkin is flushable in a toilet.

One skilled in the relevant art will recognize that many possible modifications and combinations of the disclosed embodiments may be used, while still employing the same basic underlying mechanisms and methodologies. The foregoing description, for purposes of explanation, has been written with references to specific embodiments. However, the illustrative discussions above are not intended to be exhaustive or to limit the invention to the precise forms disclosed. Many modifications and variations are possible in view of the above teachings. The embodiments were chosen and described to explain the invention and their practical applications, and to enable others skilled in the art to best utilize the invention and various embodiments with various modifications as suited to the particular use contemplated.

What is claimed is:

1. A menstrual pad, comprising:
   an interior layer includes an excretion area, wherein the excretion area includes an opening configured to drain menstrual fluid of a user away from the interior layer;
   a middle layer configured to house a menstrual fluid collection unit, wherein the menstrual fluid collection unit is configured to sanitize the menstrual fluid drained from the interior layer and to store the sanitized menstrual fluid to one or more menstrual napkins in the middle layer;
   an exterior layer configured to conceal and prevent leakage from the middle layer of the menstrual pad; and
   a support frame configured to hold the interior layer, the middle layer and the exterior layer of the menstrual pad together.

2. The menstrual pad of claim 1, wherein the interior layer is made of a hydrophobic material configured to repel the menstrual fluid of the user to the middle layer through the opening.

3. The menstrual pad of claim 1, wherein the interior layer further comprises:
   a menstrual fluid drain guide configured to drain the menstrual fluid away from the interior layer; and
   a barrier shield configured to prevent the menstrual fluid from touching anus of the user.

4. The menstrual pad of claim 1, wherein the support frame is further configured to provide an air gap between the excretion area of the interior layer and a genital area of the user, and wherein the support frame is made of polydimethylsiloxane rubber or thermoplastic elastomers, and is configured to wrap around the crotch area of the user to prevent leakage.

5. The menstrual pad of claim 1, wherein the support frame is configured to fold or unfold in a first direction to provide access to the menstrual fluid collection unit in the middle layer of the menstrual pad; and wherein the support frame is further configured to fold or unfold in a second direction to wrap or unwrap the menstrual pad around the crotch area of the user.

6. The menstrual pad of claim 1, wherein the menstrual fluid collection unit comprises:
   a sanitizing unit, wherein the sanitizing unit includes a silver sheet acting as a cathode and a copper sheet acting as an anode,
   wherein the menstrual fluid in the menstrual fluid collection unit serves as an electrolyte to initiate an electrochemical corrosion reaction between the anode and the cathode, causing oxidize copper into antibacterial copper ions that sanitize the menstrual fluid.

7. The menstrual pad of claim 6, wherein the menstrual fluid collection unit further comprises:
   a menstrual fluid holder, wherein menstrual fluid holder is configured to hold the one or more menstrual napkins,
   wherein the menstrual fluid holder is made of a hydrophobic material and is configured to prevent menstrual fluid leakage.

8. The menstrual pad of claim 1, wherein the one or more menstrual napkins comprises:
   a paper pan made of carboxymethyl cellulose powder, wood fibers and room temperature water-soluble polyvinyl alcohol, wherein the paper pan includes a plurality of collection cups configured to hold biodegradable superabsorbent polymer particles, and
   wherein a used menstrual napkin is flushable in a toilet.

9. The menstrual pad of claim 1, wherein the exterior layer of the menstrual pad comprises:
   a breathable material configured to allow moisture from the middle layer to escape the menstrual pad.

10. The menstrual pad of claim 1, wherein the reusable menstrual pad is configured to be used with an open crotch underwear or to be used with a regular underwear.

11. A method of manufacturing a menstrual pad, comprising:
   forming an interior layer, wherein the interior layer includes an excretion area, wherein the excretion area includes an opening configured to drain menstrual fluid of a user away from the interior layer;
   forming a middle layer, wherein the middle layer is configured to house a menstrual fluid collection unit, wherein the menstrual fluid collection unit is configured to sanitize the menstrual fluid drained from the interior layer and to store the sanitized menstrual fluid to one or more menstrual napkins in the middle layer;
   forming an exterior layer, wherein the exterior layer is configured to conceal and prevent leakage from the middle layer of the menstrual pad; and
   forming a support frame, wherein the support frame is configured to hold the interior layer, the middle layer and the exterior layer of the menstrual pad together.

12. The method of claim 11, further comprises:
   forming the interior layer using a hydrophobic material configured to repel the menstrual fluid of the user to the middle layer through the opening.

13. The method of claim 11, wherein forming the interior layer comprises:
   providing a menstrual fluid drain guide configured to drain the menstrual fluid away from the interior layer; and
   providing a barrier shield configured to prevent the menstrual fluid from touching anus of the user.

14. The method of claim 11, wherein forming the support frame further comprises:
   providing an air gap between the excretion area of the interior layer and a genital area of the user, and wherein the support frame is made of polydimethylsiloxane rubber or thermoplastic elastomers, and is configured to wrap around the crotch area of the user to prevent leakage.

15. The method of claim 11, further comprises:
   forming the support frame to fold or unfold in a first direction to provide access to the menstrual fluid collection unit in the middle layer of the menstrual pad; and
   forming the support frame to fold or unfold in a second direction to wrap or unwrap the menstrual pad around the crotch area of the user.

16. The method of claim 11, further comprises:
   forming the menstrual fluid collection unit by providing a sanitizing unit, wherein the sanitizing unit includes a silver sheet acting as a cathode and a copper sheet acting as an anode,
   wherein the menstrual fluid in the menstrual fluid collection unit serves as an electrolyte to initiate an electrochemical corrosion reaction between the anode and the cathode, causing oxidize copper into antibacterial copper ions that sanitize the menstrual fluid.

17. The method of claim 16, wherein forming the menstrual fluid collection unit further comprises:
   providing a menstrual fluid holder configured to hold the one or more menstrual napkins,
   wherein the menstrual fluid holder is made of a hydrophobic material and is configured to prevent menstrual fluid leakage.

18. The method of claim 11, further comprises:
   forming the one or more menstrual napkins by providing a paper pan made of carboxymethyl cellulose powder, wood fibers and room temperature water-soluble polyvinyl alcohol, wherein the paper pan includes a plurality of collection cups configured to hold biodegradable superabsorbent polymer particles, and
   wherein a used menstrual napkin is flushable in a toilet.

19. The method of claim 11, further comprises:
   forming the exterior layer of the menstrual pad using a breathable material configured to allow moisture from the middle layer to escape the menstrual pad.

20. The method of claim 11, wherein the reusable menstrual pad is configured to be used with an open crotch underwear or to be used with a regular underwear.

* * * * *